(12) United States Patent
Sibert

(10) Patent No.: US 6,441,164 B2
(45) Date of Patent: Aug. 27, 2002

(54) WURSTER'S CROWN LIGANDS

(75) Inventor: John W. Sibert, Greenville, NC (US)

(73) Assignee: East Carolina University, Greenville, NC (US)

( * ) Notice: Subject to any disclaimer, the term of this patent is extended or adjusted under 35 U.S.C. 154(b) by 0 days.

(21) Appl. No.: 09/904,332

(22) Filed: Jul. 12, 2001

Related U.S. Application Data

(62) Division of application No. 09/390,444, filed on Sep. 7, 1999, now Pat. No. 6,262,258.
(60) Provisional application No. 60/099,436, filed on Sep. 8, 1998.

(51) Int. Cl.$^7$ .................. C07D 225/00; C07F 15/02; C07F 15/04; C07F 15/06
(52) U.S. Cl. .................. 540/469; 540/450; 540/465; 556/138; 556/146
(58) Field of Search .................. 540/450, 465, 540/469; 556/138, 146

(56) References Cited

U.S. PATENT DOCUMENTS 5,445,762 A * 8/1995 Manero et al. ............. 252/299

FOREIGN PATENT DOCUMENTS

EP 528415 * 2/1993

OTHER PUBLICATIONS

Wurster, C. Ber. Dtsch. Chem. Ges., 1879, 12, pp. 522–528.
Wurster, C. Ber. Dtsch. Chem. Ges., 1879, 12, pp. 2071–2072.
Wurster, C.; Schobig, E. Ber. Dtsch. Chem. Ges., 1879, 12, 1807–1815.
Kuhn, R.; Katz, H. Z. Agnew. Chem., 1933, 46, pp. 478–479.
Bradshaw, J. S. et al.; In Comprehensive Supramolecular Chemistry; Gokel, G. W., Ed.; Pergamon Press: New York, 1996, vol. 1, pp. 35–95.
Beer, P. D. et al.; Mechanisms of Electrochemical Recognition of Cations, Anions and Neutral Guest Species by Redox–Active Receptor Molecules, *Coordination Chemistry Reviews* 185–186(1999) pp. 3–36.
Beer, P. D; Transition Metal and Organic Redox–Active Macrocycles Designed to Electrochemically Recognize Charged and Neutral Guest Species, *Advances in Inorganic Chemistry*, 39:79–157.
Beer et al; Redox–resp. crown ethers cont. a direct link . . . JCS, Dalton Trans. 11, 3295–3300 (Sep. 1997).
J.W. Siebert et al; "Wurster's cro." A new Cl. of Reox–active Lig. 214 ACS Natl. Meet. Sep. 7, 1997 abs.
Tunoglu et al; The immobi. of ionic & neutral crown eth. dyes to sp. anionic poly.. J. Mac Sc. 4, 637 (Apr. 1998).
Karabocec et al; A New vici.–diox & its . . . complex,, Trans. Met. Che (Lon) 22/4. 420–424, (Apr. 1997).
Kimura et al; Cat.–Compl.–induced aggre. & spe. ion cond. J. Inclus. Phen. Mol. Reco., Ch3, 273 (Mar. 1992).
Tunoglu, Nazan et al; The Immobilzn. of ionic & neutral crown . . . J. Mac. Sc. P&A Ch. 35/4, 637 (Apr. 1998)

* cited by examiner

*Primary Examiner*—Richard L. Raymond
*Assistant Examiner*—Sudhaker B. Patel
(74) *Attorney, Agent, or Firm*—Myers Bigel Sibley & Sajovec

(57) ABSTRACT

Wurster's crown ligands comprise a macrocyclic ligand such as a crown ether in which a hetero atom is substituted with a 1,4-phenylenediamine group. The phenylenediamine group is covalently bound to the macrocyclic ligand by one or both of the amine nitrogens, the amine nitrogen thereby substituting for the hetero atom of the macrocyclic ligand. The resulting compounds are redox active. Methods of making and using the compounds are also disclosed.

15 Claims, No Drawings

WURSTER'S CROWN LIGANDS

CLAIM FOR PRIORITY AND CROSS-REFERENCE TO OTHER APPLICATIONS

This application claims priority to and is a divisional of application Ser. No. 09/390,444, filed Sep. 7, 1999, now U.S. Pat. No. 6,262,258, which claims priority from Provisional Application Ser. No. 60/099,436, filed Sep. 8, 1998, the disclosures of which are hereby incorporated herein by reference.

FIELD OF THE INVENTION

The present invention relates to substituted crown ligands that are redox active, and methods of using the same.

BACKGROUND OF THE INVENTION

Macrocyclic polyethers, generally known as "crown ethers", were first described by Charles Pedersen. See generally C. J. Pederson, *J. Am. Chem. Soc.* 89:26, 7017 (Dec. 20, 1967). Numerous variations have been made to produce a group of compounds known as crown ligands or macrocyclic ligands.

The attachment of redox centers to crown ethers was first described by Dr. Fritz Vogtle. Such compounds are of interest because the coordinating ability (binding strength and/or selectivity) can be altered by physical or chemical means. Redox active macrocyclic ligands that have been produced to date include ferrocene derivatives, tetrathiafulvalene derivatives, and quinone derivatives. See generally P. Beer, *Chem. Soc. Rev.* 18, 409 (1989); P. Beer., *Chem. Soc. Rev.* 39, 79 (1992); T. Jorgensen et al., *Chem. Soc. Rev.* 23, 41 (1994); R. Dieing et al., *J. Chem. Soc., Perkin Trans.*, 1587 (1996); Z. Chen and L. Echegoyen, in *Crown Compounds Toward Future Applications*, p. 27 (S. Cooper Ed. 1992).

SUMMARY OF THE INVENTION

Redox active macrocyclic ligands of Formula 1A and Formula 1B are disclosed:

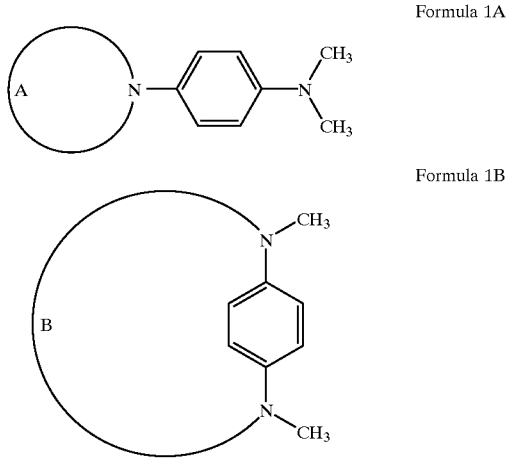

Formula 1A

Formula 1B

In Formulas 1A and 1B, the rings A and B, respectively, are not indicative of any specific number of bonds or atoms, but instead represent the ring system of a macrocyclic ligand (e.g., a crown ether) substituted with a 1,4-phenylenediamine group as shown. As noted below, the methyl groups shown may be replaced with other C1–C4 loweralkyl groups.

A second aspect of the invention is a composition comprising a redox active compound as given above in a carrier solution.

Compounds of Formulas 1A and 1B and compositions containing the same are useful as redox switches, sensors, transport agents, and electrocatalysts.

DETAILED DESCRIPTION OF THE PREFERRED EMBODIMENTS

The present invention now will be described more fully hereinafter with reference to the accompanying drawings, in which preferred embodiments of the invention are shown.

The term "macrocyclic ligand" as used herein means a macrocyclic molecule of repeating units of carbon atoms and hetero atoms (e.g., O, S, or NH), separated by the carbon atoms (generally by at least two or three carbon atoms). Macrocyclic ligands exhibit a conformation with a so-called hole capable of trapping ions or molecules, particularly cations, by coordination with the electrons of the hetero atom (e.g., a lone pair of electrons on the oxygen atoms when the hetero atoms are oxygen). In general, the macrocyclic ring contains at least 9, 12 or 14 carbon atoms and hetero atoms (e.g., O, S, NH), each hetero atom in the ring being separated from adjoining hetero atoms in the ring by two or more carbon atoms. The macrocyclic ring may be substituted or unsubstituted, and may be fused to additional rings (e.g., 1 to 4 additional rings such as phenylene, naphthylene, phenanthrylene, and anthrylene rings).

The term "crown ether" as used herein means a macrocyclic polyether whose structure exhibits a conformation with a so-called hole capable of trapping cations by coordination with a lone pair of electrons on the oxygen atoms (McGraw-Hill *Dictionary of Scientific and Technical Terms* (3d ed. 1984)). Crown ethers are a species of macrocyclic ligand.

The present invention may be carried out by substituting at least one hetero atom of a macrocyclic ligand or crown ether with a 1,4-phenylenediamine group by covalent bond to one, or both, of the amine nitrogen atoms, as shown above and below.

Any macrocyclic ligand or crown ether can be substituted as shown herein and used to carry out the present invention, including but not limited to those described in U.S. Pat. Nos. 5,252,733; 5,589,446; 5,587,499; 5,536,577; 5,478,953; 5,391,628; 4,876,367; 4,777,270; 4,652,399; 4,254,034; 4,104,275; 4,031,111; 4,024,158; 4,001,279; 3,997,562; 3,997,565; 3,987,061; and 3,687,978; the disclosures of which applicants specifically intend to be incorporated herein by reference in their entirety. The term "macrocyclic ligand" as used herein encompasses macrobicyclic ligands as well.

In general, compounds of the invention are prepared by combining N,N-dimethyl-1,4-p-phenylenediamine (for compounds of Formula 1A) or N,N'-dimethyl-1,4-p-phenylenediamine (for compounds of Formula 1B) with an acyclic precursor for a macrocyclic ligand (e.g., a polyether, polythioether, or polyaza fragment) (also called a di-substituted fragment) that is end-terminated on both ends with a sulfonate or halide (e.g., bromide, chloride or iodide, in that order of preference). The combination is carried out in a polar aprotic solvent such as acetonitrile or N,N-dimethylformamide under basic conditions, preferably with heat, to produce the compound of Formula 1A or 1B.

Acyclic precursors useful for carrying out the method may be generally represented by the formula Z—Y—Z, wherein Z is a sulfonate or halide group as described above, and Y is a macrocyclic ligand fragment such as a polyether, polythioether, or polyaza group that contains at least 8 or 11 carbon and hetero atoms, up to 120, 160, 200, 400, or 800 or more carbon and hetero atoms.

Examples of redox active macrocyclic ligands of the present invention are compounds of Formula 2:

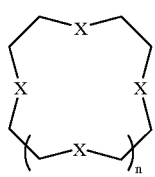

Formula 2 wherein:

X is O, S, or NH and n is 1, 2 or 3 to 6, 10, 20, 30 or 40, subject to the proviso that at least one of X is a redox active substituent selected from the group consisting of:

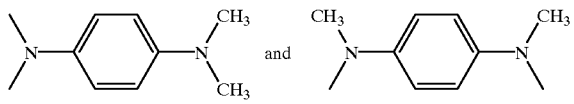

Preferably, X is O. Preferably, 1, 2, 3 or 4 of X is a redox active substituent as given above. Preferably, where more than one redox active substituent is present, the redox active substituents are the same.

In Formula 2, the C2 alkylene groups shown between hetero atoms X may be replaced with different alkylene groups (e.g., C3 or C4 alkylene groups). All of the alkylene groups in the ring system may be the same, or they may differ. The resulting ring system may be symmetric or asymmetric. The alkylene groups may be unsubstituted or substituted (e.g., they may be substituted with any of the groups shown in the patents incorporated by reference above).

Compositions of the present invention comprise a redox-active compound as described above in a carrier liquid (e.g., an aqueous carrier solution, preferably one containing at least about 30, 40 or 50 percent by weight of water). The redox-active compound may be included in the composition in any suitable amount, which will vary depending upon the use of the composition, but is typically included in an amount of from about 0.001, 0.01, or 0.1 to 5, 10, 20 or 40 percent by weight of the total composition.

As discussed in greater detail below, the redox-active compounds of the present invention have a variety of applications, including but not limited to use as redox switches, sensors, transport agents and electrocatalysts. In general, the compounds are useful in binding substrates (e.g., metals, particularly metal ions such as anions and cations), by contacting a redox active compound of the invention to a substrate that is selectively bound by or coordinates with that compound. The contacting step may be carried out under any suitable conditions depending upon the particular application. For example, the contacting step may be carried out in a liquid solution such as an aqueous solution described above. The substrate may be included in the solution in any suitable amount (e.g., from about 0.01, 0.001, 0.0001, 0.00001, 0.000001 percent by weight or less, up to about 1, 5, 10 or 20 percent by weight or more, depending upon the particular application). As will be appreciated, the binding of the substrate may be manipulated by oxidizing or reducing the redox active compound before or after the binding step. For example, the redox active compound may be oxidized before the binding step and then reduced after the binding step, or the redox active compound may be reduced before the binding step and oxidized after the binding step. Oxidation and reduction can be carried out by physical and/or chemical techniques known or apparent to those skilled in the art. Again, the particular manipulations of the redox active compound will depend upon the particular application for which the method is employed.

Ion/molecule sensors. The compounds of the present invention are useful as ion or molecule sensors. The host or macrocyclic component of the compound can be selected to bind or accommodate a particular cationic, anionic, and/or neutral guest compound. Once bound, the presence of the guest compound can be "sensed" or indicated by the redox-active-p-phenylenediamine moiety. The compound can thus be used as an analytical tool for the sensing or detection of neutral or charged guest compounds. The mode of sensing is primarily electrochemical. However, because the p-phenylenediamine moiety is a chromophore (i.e., a light absorbing unit), the ability of the compounds to absorb and emit light can also be used in sensing activity, where absorbance, transmittance, or reflectance properties of the compound are altered depending on whether or not a guest compound to be sensed is bound thereby.

Ion/molecule transport. The compounds of the invention can be oxidized reversibly in two successive steps to form a radical cation and dication, respectively. Of particular use is the first oxidation to form a radical cation, which occurs at low potential. A feature of the compounds of the invention is that their ability to bind a guest depends on which state the crown is in. Thus, these compounds have the ability to bind a guest while in a high affinity state for that particular guest, transport the guest through an appropriate medium, and, following the electrochemical switching of the crown to a low affinity state for the guest, release the guest compound. Because the host or macrocyclic component of the compound can be selected to accommodate a tremendous variety of guest compounds, there is the ability to design transport agents for a plethora of chemical species.

Redox switchable catalysis. The key to the function of a metal-containing catalyst lies in the coordination environment around the metal center. In other words, the types of atoms that are bonded to a metal and their spatial arrangement dictate the catalytic properties of a particular metal center. Because the compounds of the invention can be electrochemically "switched" between a neutral state and a radical cation, the coordination environment about a bound metal center can be altered when compounds of the present invention are bound thereto. It is through the electrochemically-modified coordination environment that the function or catalytic activity of the metal center can be affected. In principle, chemical reactions can be accelerated or decelerated depending on the state of the compound of the invention (neutral or cationic). Thus, catalysis can be controlled at the molecular level using compounds of the present invention. Importantly, because there are numerous examples of crowns or macrocycles that contain metal ions and are catalytically active in the chemical literature, numerous compounds can be produced that are not only catalysts, but under the control of a molecular switch.

Redox switchable magnetic materials. Through the linking of paramagnetic metal ions in compounds of the invention, the magnetic coupling of the metal centers is controlled by the state (neutral or radical cation) in which the compound of the invention exists. The application here permits the design of materials that display magnetic behavior that can be switched "on" or "off".

Magnetic resonance imaging contrast agents. The compounds of the invention may be introduced into the body of a living subject such as a human or animal (e.g., dog, cat, horse, cow; preferably mammalian) subject by parenteral administration into a desired site or location, and "site-oxidized" by electrodes to enhance the imaging of tissues or fluids by magnetic resonance.

While the methods, formulas and compounds described herein have been illustrated with methyl groups on the amines of the 1,4-phenylenediamine units, it will be appreciated that other C1 to C4 loweralkyl groups such as ethyl, propyl, or butyl, can also be employed and substituted therefore.

The present invention is explained in greater detail in the following non-limiting examples.

EXAMPLE 1

Preparation of "end-on" Wurster's Crown (1)

To a room temperature, stirred solution of N,N-dimethyl-1,4-p-phenylenediamine (0.880 g; 6.47 mmol) in acetonitrile (250 mL) was added anhydrous sodium carbonate (3.7 g) followed by hexaethylene glycol di-p-toluenesulfonate (3.81 g: 6.46 mmol). The mixture was then heated under a nitrogen atmosphere at reflux for 72 hours. After cooling to room temperature, the solvent was removed on a rotary evaporator and the resultant mixture partitioned between dichloromethane and water. The organic layer was separated, dried with magnesium sulfate and filtered. Pure product was obtained as a light brown oil following column chromatography on neutral or basic alumina using 0.5–1% $CH_3OH/CHCl_3$ as eluent: yield 22% of compound (1); $^1H$ NMR ($CDCl_3$) δ 2.80 (6 H, s, $CH_3$) 3.51 (4H, t, $CH_2N$), 3.66 (20 H, m, $CH_2O$), 6.72 (4 H, overlapping d, Ar); $^1H$ NMR ($CD_3CN$) δ 2.76 (6H, s, $CH_3$), 3.41 (4H, t, $CH_2N$, 3.56 (20 H, m, $CH_2O$), 6.69 (4 H, overlapping d, Ar); $^{13}C$ NMR ($CDCl_3$) δ 42.21, 51.95, 69.11, 70.55, 70.73, 114.14, 115.84, 141.78, 143.22; EI MS m/e 382 ($M^+$). $^{13}C$ NMR ($CD_3CN$) δ 42.17, 52.80, 69.80, 71.25, 71.31, 115.46, 116.33, 142.75, 144.30; EI MS m/e 382 ($M^+$).

Compound 1

EXAMPLE 2

Preparation of "side-on" Wurster's Crown (2)

To a room temperature, stirred solution of N,N'-dimethyl-1,4-p-phenylenediamine dihydrobromide (prepared by modification of the procedures of L. Michaelis et al., *J. Chem. Soc.* 1939, 61 (1981)) (1.0 g; 3.4 mmol) in acetonitrile (150 mL) was added anhydrous sodium carbonate (3.9 g) followed by hexaethylene glycol di-p-toluenesulfonate (2.0 g; 3.4 mmol). The mixture was then heated under a nitrogen atmosphere at reflux for 72 hours. After cooling to room temperature, the solvent was removed on a rotary evaporator and the resultant mixture partitioned between dichloromethane and water. The organic layer was separated, dried with magnesium sulfate and filtered. Pure product was obtained as a golden oil following column chromatography on neutral or basic alumina using 0.5–1% $CH_3OH/CHCl_3$ as eluent. Upon storage in air, the pure product darkened and developed a green cast: yield 25% of compound (2); $^1H$ NMR ($CDCl_3$) δ 2.84 (6H, s, $CH_3$), 3.39 (4 H, t, $CH_2N$), 3.55–3.65 (20 H, m, $CH_2O$), 6.78 (4 H, s, Ar): $^1H$ NMR ($CD_3CN$) δ 2.81 (6H, s, $CH_3$), 3.34 (4H, t, $CH_2N$), 3.45–3.60 (20 H, m, $CH_2O$), 6.72 (4H, s, Ar); $^{13}C$ NMR ($CDCl_3$) δ 39.44, 54.63, 68.77, 70.59, 70.83, 70.88, 70.94, 115.29, 142.44; $^{13}C$ NMR ($CD_3CN$) δ39.40, 54.93, 69.41, 71.31, 71.40, 71.44, 71.51, 115.87, 143.31; EI MS m/e 382 ($M^+$).

Compound 2

The foregoing is illustrative of the present invention, and is not to be construed as limiting thereof. The invention is defined by the following claims, with equivalents of the claims to be included therein.

What is claimed is:

1. A redox active macrocyclic ligand of Formula 1B:

Formula 1B wherein ring B represents a macrocyclic ligand; and R is C1–C4 loweralkyl.

2. A compound according to claim 1, wherein said macrocyclic ligand is a crown ether.

3. A compound according to claim 1, wherein said compound is a compound of formula 2:

Formula 2 wherein:

X is O, S, or NH; and n is 1 to 40;

subject to the proviso that at least one of X is a redox active substituent of the formula:

wherein R is C1–C4 loweralkyl.

4. A compound according to claim 3, wherein X is O.

5. A compound according to claim 3, wherein n is 1 to 10.

6. A compound according to claim 1, wherein said compound is:

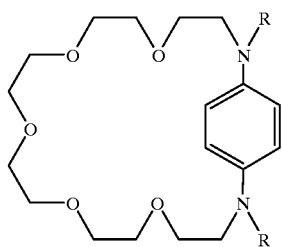

wherein R is C1–C4 loweralkyl.

7. A composition comprising a compound according to claim 1 in a carrier liquid.

8. A composition according to claim 7, wherein said carrier liquid is an aqueous carrier liquid.

9. A method of binding a substrate, comprising:

contacting a redox-active macrocyclic ligand to a substrate bound by said redox-active macrocyclic ligand, said redox active macroacrylic ligand being a compounds of Formula 1B:

Formula 1B

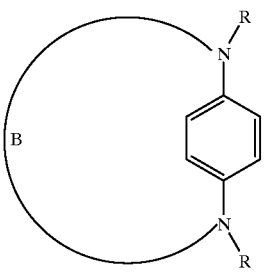

wherein ring B represents a macrocyclic ligand; and
R is C1–C4 loweralkyl.

10. A method according to claim 9, wherein said contacting step is carried out in a liquid solution.

11. A method according to claim 9, wherein said macrocyclic ligand is oxidized or reduced prior to said contacting step.

12. A method according to claim 9, wherein said macrocyclic ligand is oxidized or reduced following said contacting step.

13. A method according to claim 9, wherein said substrate is a metal.

14. A method according to claim 9, wherein said substrate is a cation.

15. A method of making a compound of Formula 1B:

Formula 1B

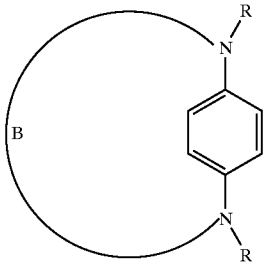

wherein ring B represents a macrocyclic ligand and R represents C1–C4 loweralkyl;

said method comprising combining N,N'-dimethyl-1,4-p-phenylenediamine with an acyclic precursor of a macrocyclic ligand, which acyclic precursor is end-terminated on both ends with a sulfonate or halide group, in a polar aprotic solvent under basic conditions to produce the compound of Formula 1B.

* * * * *